(12) United States Patent
Cho et al.

(10) Patent No.: US 11,370,923 B2
(45) Date of Patent: Jun. 28, 2022

(54) BLACK PEARLESCENT PIGMENT USING NATURAL CHARCOAL AND PRODUCTION METHOD THEREOF

(71) Applicant: CQV CO., LTD., Chungcheongbuk-do (KR)

(72) Inventors: Kum-Sung Cho, Eumseong-gun (KR); Kwang-Choong Kang, Cheongju-si (KR); Byung-Ki Choi, Cheongju-si (KR); Kwang-Soo Lim, Cheongju-si (KR); Kil-Wan Chang, Cheongju-si (KR)

(73) Assignee: CQV CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 15/576,556

(22) PCT Filed: Oct. 23, 2017

(86) PCT No.: PCT/KR2017/011710
§ 371 (c)(1),
(2) Date: Nov. 22, 2017

(87) PCT Pub. No.: WO2018/097486
PCT Pub. Date: May 31, 2018

(65) Prior Publication Data
US 2019/0002703 A1 Jan. 3, 2019

(30) Foreign Application Priority Data
Nov. 28, 2016 (KR) .................. 10-2016-0158958

(51) Int. Cl.
*A61K 8/19* (2006.01)
*C09C 3/06* (2006.01)
*A61Q 1/10* (2006.01)
*C09D 5/36* (2006.01)
*C09D 17/00* (2006.01)
*A61Q 3/02* (2006.01)
*A61Q 19/00* (2006.01)
*A61K 8/02* (2006.01)
*A61Q 1/00* (2006.01)
*A61K 8/97* (2017.01)
*C09C 1/00* (2006.01)

(52) U.S. Cl.
CPC .............. *C09C 3/063* (2013.01); *A61K 8/022* (2013.01); *A61K 8/0254* (2013.01); *A61K 8/19* (2013.01); *A61K 8/97* (2013.01); *A61Q 1/00* (2013.01); *A61Q 1/10* (2013.01); *A61Q 3/02* (2013.01); *A61Q 19/00* (2013.01); *C09C 1/0021* (2013.01); *C09C 3/06* (2013.01); *C09D 5/36* (2013.01); *C09D 17/004* (2013.01); *A61K 2800/412* (2013.01); *A61K 2800/42* (2013.01); *A61K 2800/436* (2013.01); *A61K 2800/652* (2013.01); *C01P 2004/60* (2013.01); *C01P 2004/61* (2013.01); *C01P 2006/60* (2013.01)

(58) Field of Classification Search
CPC ........ C09C 3/063; A61K 8/0254; A61K 8/19; A61K 2800/652; A61K 2800/43; A61Q 1/10; C09D 5/36; C09D 17/004; C09D 17/005; C01P 2004/60
See application file for complete search history.

(56) References Cited

U.S. PATENT DOCUMENTS

| | | | | |
|---|---|---|---|---|
| 4,076,551 A | * | 2/1978 | Bernhard | B82Y 30/00 106/417 |
| 6,004,567 A | * | 12/1999 | Marchi-Lemann | A61K 8/0241 424/401 |
| 6,210,694 B1 | * | 4/2001 | Park | A61K 8/97 424/401 |
| 2006/0013838 A1 | * | 1/2006 | Peng | A61K 8/25 424/401 |
| 2008/0302275 A1 | * | 12/2008 | Allen | B82Y 30/00 106/402 |
| 2009/0185992 A1 | * | 7/2009 | Conan | A61K 8/11 424/61 |
| 2016/0271052 A1 | * | 9/2016 | Choi | C09C 3/08 |

FOREIGN PATENT DOCUMENTS

| | | | |
|---|---|---|---|
| CN | 101760044 A | | 6/2010 |
| CN | 104962136 A | | 10/2015 |
| CN | 105916945 A | | 8/2016 |
| JP | 2008179737 A | * | 8/2008 |
| JP | 2009-209327 A | | 9/2009 |
| JP | 2012-240919 A | | 12/2012 |
| JP | 2012240919 A | * | 12/2012 |
| JP | 2014-101298 A | | 6/2014 |

(Continued)

OTHER PUBLICATIONS

Extended European Search Report dated Nov. 13, 2019 in connection with the counterpart European Patent Application No. EP17797849.1.

*Primary Examiner* — Jessica Worsham
(74) *Attorney, Agent, or Firm* — Hauptman Ham, LLP (57) ABSTRACT

The present invention relates to a technology for producing a black pearlescent pigment for cosmetics which is a human-friendly and nature-friendly by using a pigment including natural charcoal powder. The production method of the pearlescent pigment using natural charcoal according to the present invention includes (a) milling natural charcoal to produce a pigment including natural charcoal powder; and (b) coating a flake substrate with the produced pigment including the natural charcoal powder, wherein the milling is performed at 20 to 40 Hz for 24 to 72 hours, and an average particle size of the pigment including the natural charcoal powder is 100 to 300 nm.

8 Claims, 4 Drawing Sheets

(56) References Cited

FOREIGN PATENT DOCUMENTS

| JP | 5812220 B1 | 10/2015 | | |
|---|---|---|---|---|
| JP | 2016-540069 A | 12/2016 | | |
| JP | 2018-502183 A | 1/2018 | | |
| KR | 19990041767 A | * | 6/1999 | ............... A61K 7/02 |
| KR | 1020030068026 A | | 8/2003 | |
| KR | 1020070079620 A | | 8/2007 | |
| KR | 10-2011-0108401 A | | 10/2011 | |
| KR | 101541009 B1 | | 7/2015 | |
| WO | WO-2015065027 A1 | * | 5/2015 | ............... C09C 3/08 |
| WO | 2016-085874 A | | 6/2016 | |

* cited by examiner

BLACK PEARLESCENT PIGMENT USING NATURAL CHARCOAL AND PRODUCTION METHOD THEREOF

CROSS REFERENCE TO RELATED APPLICATION

This present application is a national stage filing under 35 U.S.C § 371 of PCT application number PCT/KR2017/011710 filed on Oct. 23, 2017 which is based upon and claims the benefit of priority to Korean Patent Application No. 10-2016-0158958 filed on Nov. 28, 2016 in the Korean Intellectual Property Office. The disclosures of the above-listed applications are hereby incorporated by reference herein in their entirety.

TECHNICAL FIELD

The present invention relates to a technology for producing a black pearlescent pigment, and more specifically, the present invention relates to a production method of a pearlescent pigment capable of producing a colored pigment for cosmetics using natural charcoal, and a pearlescent pigment using the same.

BACKGROUND ART

A pigment is used to have an aesthetic effect in various fields.

An organic pigment used in a pearl pigment for cosmetics has advantages in that it has a wide range of colors, is clear, and has excellent coloring power, but has disadvantages in that it is more expensive than an inorganic pigment and has problems with durability, heat resistance, etc. The organic pigment is mainly used for paints, inks, rubbers, fibers, paper, leather, cosmetics, etc.

In recent years, as environmental problems become serious, there is a tendency to prefer the inorganic pigment rather than the organic pigment.

Since the pearl pigment for cosmetics is sensitive to trends, various products are continuously released. However, the pearl pigment for cosmetics has various limitations on a raw material thereof due to environmental restriction. Accordingly, a pearl pigment for cosmetics using a new type of natural organic pigment is currently required in the market.

Cosmetics are largely divided into base makeup products that are applied all over the face and point makeup products that are applied only to a local part of the face. The point makeup products include lipstick, eye shadow, blusher, etc., and are used to give the face a luster to look beautiful. Color is the most important factor in the cosmetics used for this purpose.

A black pigment is generally produced by coating a white luster pigment with iron oxide to expresses a brownish color and depositing a blue pigment on a surface thereof to produce a black-based luster pigment, or by a black pigment including carbon black. When the black pigment as produced above is applied to the skin, allergic reactions such as urticaria, rhinitis, and asthma, etc., may be caused. Accordingly, it is necessary to develop a luster pigment for cosmetics which is human-friendly and nature-friendly by using eco-friendly natural charcoal.

As a background related to the present invention, Korean Patent Laid-Open Publication No. 10-2011-0108401 (published on Oct. 5, 2011) discloses an organic black pigment and a production method thereof.

DISCLOSURE

Technical Problem

It is an aspect of the present invention to produce a black pearlescent pigment using natural charcoal powder, and to provide a pearlescent pigment for cosmetics which is human-friendly and nature-friendly.

Technical Solution

In accordance with one aspect of the present invention, a production method of a pearlescent pigment includes: (a) milling natural charcoal to produce a pigment including natural charcoal powder; and (b) coating a flake substrate with the produced pigment including the natural charcoal powder, wherein the milling is performed at 20 to 40 Hz for 24 to 72 hours, and an average particle size of the pigment including the natural charcoal powder is 100 to 300 nm.

The step (b) may include: (b1) preparing a pigment suspension by adding a water-soluble inorganic salt solution and adjusting pH to a neutral state; (b2) forming a substrate suspension by mixing the flake substrate with D.I. water, followed by stirring and dispersing; and (b3) coating the flake substrate by mixing an acidity regulator the pigment suspension in the substrate suspension to coat a surface of the flake substrate with the natural charcoal powder.

The pigment including the natural charcoal powder may be at least any one black pigment selected from oak charcoal, bamboo charcoal, Daimyo oak charcoal, Konara oak charcoal, oriental chestnut oak charcoal, chestnut charcoal, *Quercus phillyraeoides* charcoal, Japanese larch charcoal, pine charcoal, Japanese cedar charcoal, Japanese cypress charcoal, Yukari charcoal, mangrove charcoal, sasanqua charcoal, olive charcoal, acacia charcoal, and a combination thereof.

In the preparing of the pigment suspension, a concentration of the pigment may be adjusted to 5 to 30 wt % based on 100 wt % of the suspension.

In the forming of the substrate suspension, a concentration of the substrate may be adjusted to 3 to 25 wt % based on 100 wt % of the suspension.

In the coating of the flake substrate, the substrate suspension may further include a metal salt including one selected from $BaCl_2$, $CaCl_2$, $AlCl_3$, $SnCl_4$, $TiCl_4$, $TiOCl_2$, $TiOSO_4$, $FeCl_3$, $FeSO_4$, $SiCl_4$, $ZrOCl_2$, $Na_2OSiO_2 5H_2O$, $MnCl_2$, $MgCl_2$, and $CoCl_2$, or a mixture of one or more thereof.

A concentration of the metal salt may be adjusted to 3 to 20 wt % based on 100 wt % of the suspension.

The production method may further include, after the coating of the flake substrate, washing the flake substrate by rinsing and dehydrating the flake substrate coated with the natural charcoal powder; drying the flake substrate by drying the washed flake substrate; and screening the flake substrate by separating the flake substrate formed larger than a predetermined size among the dried flake substrates, using a mesh.

The drying of the flake substrate may be performed at 60 to 150° C.

In the screening of the flake substrate, an average particle size of the flake substrate to be separated may be 45 μm or less.

In the forming of the substrate suspension, the flake substrate may include one or more of synthetic mica, natural mica, glass, plate iron oxide, plate alumina and plate silica, talc, and bismuth, or the surface of the flake substrate may be coated with a metal oxide.

In accordance with another aspect of the present invention, there is provided a black pearlescent pigment using natural charcoal in which a surface of a flake substrate is coated with a pigment including natural charcoal powder and an average particle size of the pigment including the natural charcoal powder is 100 to 300 nm.

In accordance with still another aspect of the present invention, a cosmetic includes a black pearlescent pigment using natural charcoal produced according to the production method of the present invention, and at least one of mascara, eye shadow, eyeliner, and nail.

In accordance with still another aspect of the present invention, an industrial paint includes: a black pearlescent pigment using natural charcoal produced according to the production method of the present invention, and at least one of automotive coating paint, printing ink, coloring paint, and paint for painting.

Advantageous Effects

The technology for producing the pearlescent pigment according to the present invention may be used to produce a black pearlescent pigment for cosmetics which is human-friendly and nature-friendly by using a pigment including natural charcoal powder.

Accordingly, it is possible to reduce contamination caused by organic materials in a production process of cosmetics, and the black pearlescent pigment according to the present invention may be applied to natural hypoallergenic cosmetics.

DETAILED DESCRIPTION OF MAIN ELEMENTS

S110: FORM PIGMENT SUSPENSION
S120: FORM SUBSTRATE SUSPENSION
S130: COAT FLAKE SUBSTRATE

BEST MODE

Advantages and features of the present invention and methods to achieve them will be elucidated from exemplary embodiments described below in detail with reference to the accompanying drawings. However, the present invention is not limited to exemplary embodiments disclosed herein but will be implemented in various forms. The exemplary embodiments are provided by way of example only so that a person of ordinary skilled in the art can fully understand the disclosures of the present invention and the scope of the present invention. Therefore, the present invention will be defined only by the scope of the appended claims. Like reference numerals refer to like components throughout the specification.

Hereinafter, a black pearlescent pigment using natural charcoal and a production method thereof according to preferable exemplary embodiments of the present invention will now be described in more detail with reference to the accompanying drawings.

Figure 1:
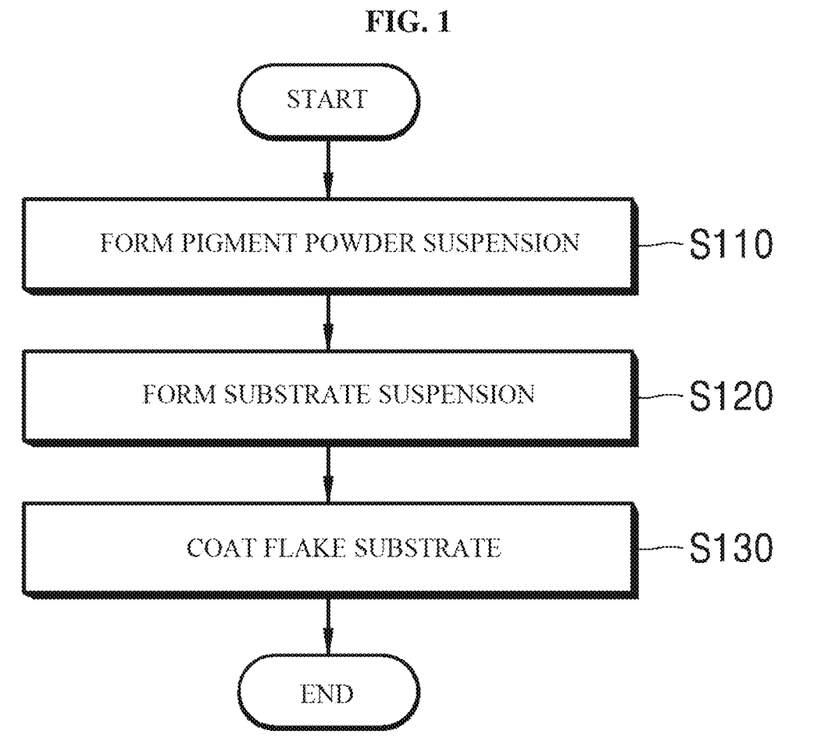
FIG. 1 is a flowchart illustrating a production process of a pearlescent pigment using natural charcoal powder according to an exemplary embodiment of the present invention.

FIG. 1 is a flowchart illustrating a production process of a pearlescent pigment using natural charcoal powder according to an exemplary embodiment of the present invention.

Referring to FIG. 1, a production method of a black pearlescent pigment according to an exemplary embodiment of the present invention includes forming a pigment suspension S110, forming a substrate suspension S120, and coating a flake substrate S130.

Step of Forming Pigment Suspension S110

A pigment including natural charcoal powder is produced by milling natural charcoal, a water-soluble inorganic salt solution is added thereto, and pH is adjusted to a neutral state to prepare a pigment suspension.

The milling is performed to form nano-sized natural charcoal powder from the natural charcoal, and for example, may be performed by ball milling, dry milling, or the like.

In the present invention, it is possible to obtain powder having a nano-sized particle diameter of 100 to 300 nm by milling the natural charcoal using frequency (Hz) which means the number of vibrations per second. As the particle size of the powder satisfies the nano-size, adhesion property of the pigment to a substrate and blackness are improved, and excellent color is exhibited while maintaining a function equal to or more than that of a commonly used cosmetic pigment.

Further, the milling using frequency provides an effect of improving dispersion stability of the pigment and spreadability after formulation as compared to milling using revolutions per minute (rpm) which represents the number of revolutions per minute.

The milling may be performed at 20 to 40 Hz for 24 to 72 hours. When time for the milling is less than 24 hours, dispersion of the pigment may be insufficient. When the time for the milling is more than 72 hours, the process time may be lengthened without further dispersion effect, and thus, efficiency may be lowered.

By milling the natural charcoal, it is possible to form a pigment including the natural charcoal powder having a nano size, and an average particle size of the pigment is preferably 100 to 300 nm. When the average particle size of the pigment is less than 100 nm, there may be no improvement in saturation (blackness) after a surface of the substrate is coated with the pigment including the powder. On the other hand, when the average particle size is more than 300 nm, the size of the pigment is large, and thus, adhesion property to the substrate may be poor, and the blackness may decrease after the reaction.

The pigment including the natural charcoal powder may be at least any one black pigment selected from oak charcoal, bamboo charcoal, Daimyo oak charcoal, Konara oak charcoal, oriental chestnut oak charcoal, chestnut charcoal, *Quercus phillyraeoides* charcoal, Japanese larch charcoal, pine charcoal, Japanese cedar charcoal, Japanese cypress charcoal, Yukari charcoal, mangrove charcoal, sasanqua charcoal, olive charcoal, acacia charcoal, and a combination thereof.

The water-soluble inorganic salt solution may include one selected from NaOH, KOH, Ca(OH)$_2$, NH$_3$, Mg(OH)$_2$, CH$_3$NH$_2$, CH$_3$CH$_2$NH$_2$, CH$_3$OH, Al(OH)$_3$, and AlCl$_3$, or a mixture of one or more thereof.

In the preparing of the pigment suspension, a concentration of the pigment is preferably adjusted to 5 to 30 wt % based on 100 wt % of the suspension. When the concentration of the pigment is less than 5 wt %, milling efficiency at the time of milling may be lowered due to the low concentration. On the other hand, when the concentration of the pigment is more than 30 wt %, an amount of the pigment including the powder relative to the solution may be excessively large, and thus, the milling efficiency may be lowered.

Step of Forming Substrate Suspension S120

Next, a substrate suspension is formed by mixing a flake substrate with D.I. water, followed by stirring and dispersing. The flake substrate may include one or more of synthetic mica, natural mica, glass, plate iron oxide, plate alumina and plate silica, talc, and bismuth. Alternatively, the surface of the flake substrate may be coated with a metal oxide to further improve heat resistance of the pigment. As the metal oxide, for example, TiO$_2$, Fe$_2$O$_3$, Cr$_2$O$_3$, SiO$_2$, ZnO, ZnO$_2$, Ce$_2$O$_3$, MgO, and Al$_2$O$_3$, etc., may be used.

In addition, the flake substrate may include the above-described components, and at the same time the metal oxide may be coated on the surface of the substrate.

Here, the stirring and dispersing may be performed at 200 to 500 rpm for a predetermined time.

In the forming of the substrate suspension, a concentration of the substrate may be adjusted to 3 to 25 wt % based on 100 wt % of the suspension. When the concentration of the substrate is less than 3 wt %, the concentration may be excessively low to thereby lower the reaction efficiency. When the concentration of the substrate is more than 25 wt %, aggregation may occur due to the high concentration of the substrate suspension.

Step of Coating Flake Substrate S130

Next, the surface of the flake substrate is coated with the natural charcoal powder by mixing an acidity regulator with the pigment suspension in the substrate suspension.

The acidity regulator includes an acidic solution including one selected from hydrochloric acid, sulfuric acid, acetic acid, etc., which exhibits acidity, or a mixture of one or more thereof.

The substrate suspension may further include a metal salt including one selected from BaCl$_2$, CaCl$_2$), AlCl$_3$, SnCl$_4$, TiCl$_4$, TiOCl$_2$, TiOSO$_4$, FeCl$_3$, FeSO$_4$, SiCl$_4$, ZrOCl$_2$, Na$_2$OSiO$_2$5H$_2$O, MnCl$_2$, MgCl$_2$, and CoCl$_2$, or a mixture of one or more thereof.

A concentration of the metal salt may be adjusted to 3 to 20 wt % based on 100 wt % of the suspension. When the concentration of the metal salt is less than 3 wt %, an amount of the solution to be added may be large, and thus, the efficiency may be lowered. When the concentration is more than 20 wt %, a coated state of the substrate after the reaction may be lowered due to the rapid pH change.

The coating of the flake substrate may be performed at 100 to 500 rpm.

When the rpm is less than 100 rpm, a dispersion effect at the time of the reaction may be lowered and the pigments may be aggregated. When the rpm is 500 rpm or more, only the rpm may be increased without further dispersion effect, and thus, the efficiency may be lowered.

The production method may further include, after the coating of the flake substrate, washing the flake substrate by rinsing and dehydrating the flake substrate coated with the natural charcoal powder; drying the flake substrate by drying the washed flake substrate; and screening the flake substrate by separating the flake substrate formed larger than a predetermined size among the dried flake substrates, using a mesh.

The drying of the flake substrate may be performed at 60 to 150° C. When the temperature is less than 60° C., time for the drying may be excessively long, resulting in a decrease in productivity. When the temperature is more than 150° C., aggregation may occur due to the rapid drying time.

In the screening of the flake substrate, an average particle size of the flake substrate to be separated may be 45 μm or less.

In the screening of the flake substrate, agglomerated particles formed during the reaction may be removed using a mesh.

According to the present invention, it is possible to provide a production method of a pearlescent pigment which is human-friendly and nature-friendly by using natural charcoal powder, and to provide a pearlescent pigment for cosmetics produced through such a production technique.

Accordingly, it is possible to replace conventional organic pigments with the natural pigment including natural charcoal powder, thereby reducing contamination caused by organic materials in a production process of cosmetics, and the natural pigment according to the present invention may be applied to natural hypoallergenic cosmetics.

The cosmetics may include at least one of mascara, eye shadow, eyeliner, and nail, and these are characterized by including the black pearlescent pigment produced according to the production method of the present invention.

Further, since the black pearlescent pigment produced according to the production method of the present invention is excellent in hiding power and heat resistance, it is able to be used as an industrial paint. The industrial paint may include, for example, at least one of automotive coating paint, printing ink, coloring paint, and paint for painting.

Specific examples of the black pearlescent pigment using natural charcoal and the production method thereof as described above are as follows.

1. Production of Pearlescent Pigment 10 g of bamboo charcoal and 90 g of primary distilled water were added to a 250 ml bottle for ball milling to perform ball milling at 35 Hz for 48 hours, thereby producing a pigment including natural charcoal powder having an average particle size of 100 to 300 nm. (The pigment including the charcoal powder in the solution had a concentration of 10 wt %.)

Figure 2:
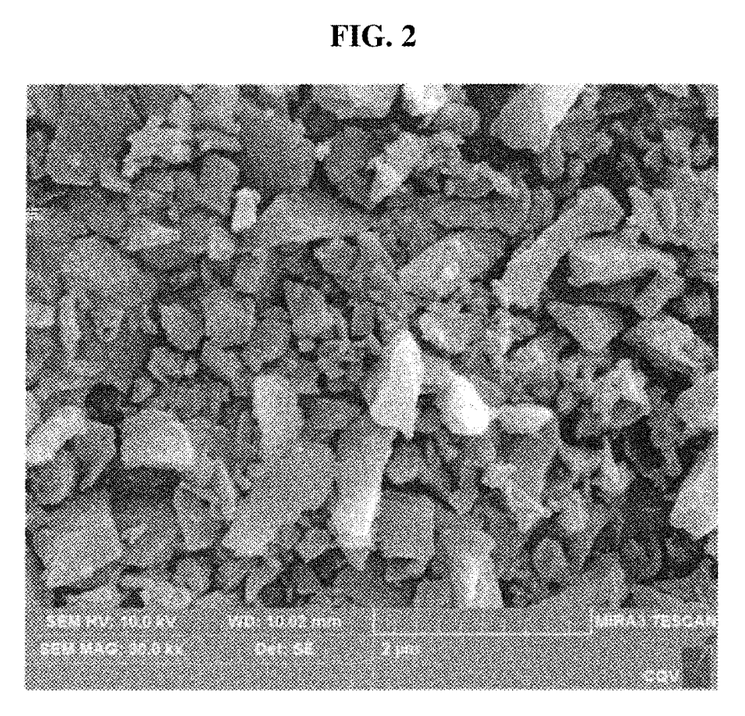
FIG. 2 is an SEM image illustrating a pigment including natural charcoal powder before milling according to an exemplary embodiment of the present invention.
Figure 3:
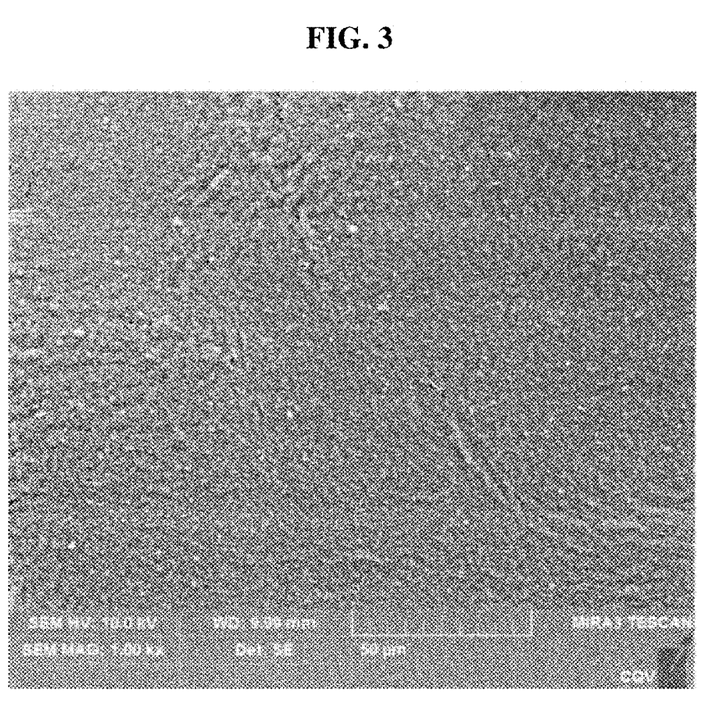
FIG. 3 is an SEM image illustrating a pigment including natural charcoal powder after milling according to an exemplary embodiment of the present invention.

FIGS. 2 and 3 are SEM images illustrating the pigment including natural charcoal powder before and after milling according to an exemplary embodiment of the present invention, respectively.

Next, the produced pigment was mixed with sodium hydroxide, which is a water-soluble inorganic salt solution so that pH was adjusted to 7, thereby preparing a pigment suspension.

Then, 30 g of plate alumina as the flake substrate and 270 g of primary distilled water were added to a 2 L beaker, followed by stirring and dispersing at 20 to 25° C. at 300 rpm, thereby forming a substrate suspension. Next, 10% sodium hydroxide solution was added to the pigment suspension so that the pH was adjusted to pH 12, and the mixture was mixed with the substrate suspension together with AlCl$_3$ solution having a concentration of 5 wt % to thereby maintain the pH to 5.5. The reaction was completed by stirring for 10 minutes, followed by rinsing and dehydrating, and then, dried at 120° C. for 2 hours. The dried flake substrate was screened using a mesh, and the flake substrates formed larger than a predetermined size were separated or aggregated particles formed during the reaction were removed.

As a result, the surface of the flake substrate was coated with the natural charcoal powder to produce a black pearlescent pigment.

Figure 4:
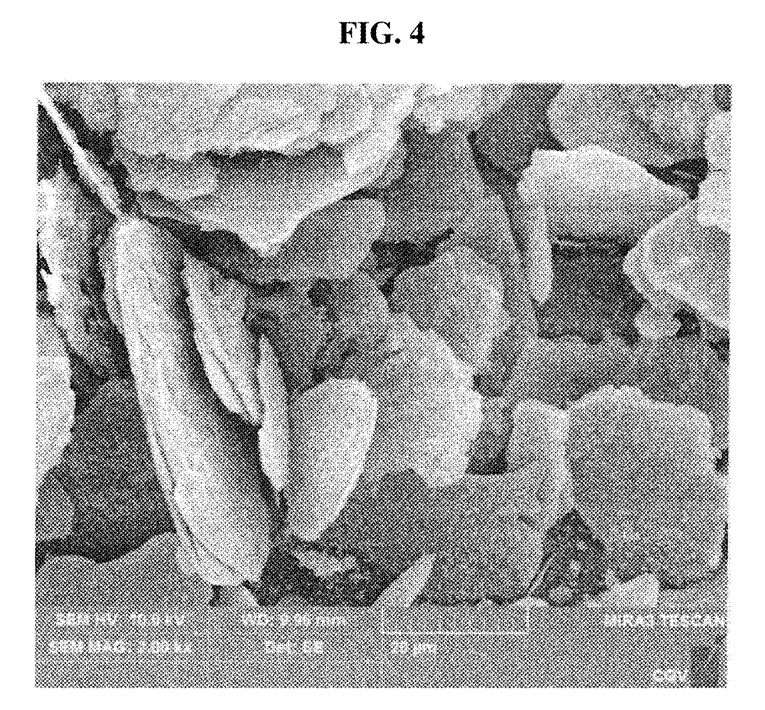
FIG. 4 is an SEM image of a pearlescent pigment in which a substrate is coated with a pigment including bamboo charcoal powder which is produced according to an exemplary embodiment of the present invention.

FIG. 4 is an SEM image of a pearlescent pigment in which a substrate is coated with a pigment including bamboo charcoal powder which is produced according to an exemplary embodiment of the present invention.

2. Cosmetics to which Pearlescent Pigment is Applied

The black pearlescent pigment produced according to the Example of the present invention may be applied to cosmetics including at least one of mascara, eye shadow, eyeliner, and nail.

[Table 1] shows the composition of the mascara to which the pearlescent pigment produced according to the Example is applied.

TABLE 1

| Raw material name | Content |
|---|---|
| Cetearyl alcohol | 2.00 |
| PEG20 Glyceryl stearate | 1.50 |
| Beads wax | 11.00 |
| Stearic acid | 8.00 |
| Black iron oxide | 3.00 |
| Preservative | 0.50 |
| Pearlescent pigment | 7.00 |
| Butylene glycol | 2.00 |
| Acrylate copolymer | 30.00 |
| Polyvinyl alcohol | 3.00 |
| Triethanolamine | 3.00 |
| D.I. water | 29.00 |
| Total | 100.00 |

[Table 2] shows the composition of the eye shadow to which the pearlescent pigment produced according to the Example is applied.

TABLE 2

| Raw material name | Content |
|---|---|
| Pearlescent pigment | 10.00 |
| Talc | 68.40 |
| Mica | 7.20 |
| Zinc stearate | 5.40 |
| Silica | 4.50 |
| Methyl methacrylate copolymer | 2.88 |
| Titanium dioxide | 1.44 |
| Aluminum myristate | 0.09 |
| Triethoxycaprylylsilane | 0.05 |
| Dimethicone | 0.04 |
| Total | 100.00 |

[Table 3] shows the composition of the liquid type eyeliner to which the pearlescent pigment produced according to the Example is applied.

TABLE 3

| Raw material name | Content |
|---|---|
| D.I. water | 32.87 |
| Butylene glycol | 1.00 |
| Sodium polyacrylate | 1.00 |
| Disodium EDTA | 0.03 |
| Black iron oxide | 10.00 |
| Pearlescent pigment | 14.00 |
| Silica | 0.50 |
| Preservative | 0.60 |
| Silicone oil | 2.00 |
| Caprylic/Capric triglyceride | 2.00 |
| Diisostearyl malate | 2.00 |
| Cetearyl olivate/Sorbitan olivate | 2.00 |
| Polyoxyethylene lauryl ether | 2.00 |
| Acrylate copolymer | 30.00 |
| Total | 100.00 |

[Table 4] shows the composition of the gel type eyeliner to which the pearlescent pigment produced according to the Example is applied.

TABLE 4

| Raw material name | Content |
|---|---|
| Ceresin | 18.00 |
| Sodium polyacrylate | 3.00 |
| Silicone acrylate | 2.00 |
| Cyclomethicone | 10.70 |
| Silicone oil | 3.00 |
| Preservative | 0.30 |
| Isododecane | 10.00 |
| Caprylic/Capric triglyceride/ Stearalkonium hectorite/ Propylene carbonate | 33.00 |
| Pearlescent pigment | 20.00 |
| Total | 100.00 |

[Table 5] shows the composition of the nail to which the pearlescent pigment produced according to the Example is applied.

TABLE 5

| Raw material name | Content |
|---|---|
| Pearlescent pigment | 3.00 |
| Nitrocellulose (1/2 second) | 10.00 |
| Alkyd resin | 10.00 |
| Acetyl tributyl citrate | 2.00 |
| Ethyl acetate | 20.00 |
| Butyl acetate | 15.00 |
| Ethyl alcohol | 5.00 |
| Toluene | 35.00 |
| Total | 100.00 |

Properties such as spreading ability, hiding power, color, matte feeling, etc., of the cosmetics produced with the compositions described in [Table 1] to [Table 5] above are shown in [Table 6] below.

TABLE 6

| Type of cosmetics | Spreadability | Hiding power | Color | Matte feeling |
|---|---|---|---|---|
| Mascara | ⊙ | ⊙ | ⊚ | ⊙ |
| Eye shadow | ⊚ | ⊚ | ⊚ | ⊚ |
| Eyeliner (liquid type) | ⊙ | ⊚ | ⊙ | ⊚ |
| Eyeliner (gel type) | ⊙ | ⊙ | ⊚ | ⊙ |
| Nail | ⊙ | ⊙ | ⊚ | ⊚ |

X (less than 60 points): Bad
Δ (60 to 69 points): Medium
○ (70 to 79 points): Relatively good
⊚ (80 to 89 points): Excellent
⊙ (90 to 100 points): Extremely excellent To evaluate spreadability, hiding power, color and matte feeling of each product, [Table 6] shows results obtained by performing a sensory evaluation (0 to 100 points) including feeling of use as a cosmetic, etc., on 40 female panelists from 20 to 40 years old to determine scores and evaluating sections to which its average value is included.

Referring to [Table 6] above, it may be confirmed that when the pigment produced according to the Example is used as a cosmetic pigment, spreadability, hiding power, transparency and excellent color are exhibited. It means that when the pearlescent pigment according to the present invention is used, it is possible to express colors by low gloss while maintaining a function equal to or more than that of a commonly used cosmetic pigment.

3. Industrial Paint to which the Pearlescent Pigment is Applied

The black pearlescent pigment produced according to the Examples of the present invention may be applied to an industrial paint including at least one of automotive coating paint, printing ink, coloring paint, and paint for painting.

[Table 7] shows the composition of the paint to which the pearlescent pigment produced according to the Example is applied.

TABLE 7

| Raw material name | Content |
| --- | --- |
| Pearlescent pigment | 20 |
| Hydroxypropylmethylcellulose | 10 |
| Stearic acid | 10 |
| Ethyl alcohol | 40 |
| Toluene | 20 |
| Total | 100 |

TABLE 8

| Paint type | Hiding power | Heat resistance |
| --- | --- | --- |
| Automotive coating paint | ⊙ | ⊙ |

☐ (90 to 100 points): Extremely excellent

Table 8 shows results of hiding power and heat resistance after coating the paint produced in [Table 7] on the surface of automotive steel plate (JISG3310), followed by curing at 200° C. for 30 minutes.

Referring to [Table 8], it may be confirmed that when the pigment produced according to the Example is included and applied to an industrial paint, the paint has excellent hiding power and heat resistance. It means that the pearlescent pigment according to the present invention exhibits the function equal to or more than that of the commonly used industrial paint.

Therefore, the technology for producing the pearlescent pigment according to the present invention may produce the black pearlescent pigment for cosmetics which is a human-friendly and nature-friendly by using the pigment including the natural charcoal powder. Accordingly, it is possible to reduce contamination caused by organic materials in a production process of cosmetics, and the black pearlescent pigment according to the present invention may be applied to natural hypoallergenic cosmetics.

Further, the pearlescent pigment of the present invention is excellent in hiding power and heat resistance to be capable of being applied to industrial paints such as automotive coating paint, printing ink, coloring paint, and paint for painting.

While Examples of the present invention have been described with reference to the accompanying drawings, the present invention is not limited to the above-described Examples, but may be formed in various forms. It will be understood by those skilled in the art that other specific forms may be made without departing from the technical idea or essential features of the present invention. Therefore, it is to be understood that exemplary embodiments described hereinabove are illustrative rather than being restrictive in all aspects.

The invention claimed is:

1. A production method of a pearlescent pigment comprising:
preparing a pigment comprising a natural charcoal powder, comprising milling a natural charcoal to produce the natural charcoal powder having an average particle size ranging from 100 nm to 300 nm; and
coating a flake substrate with the pigment, comprising:
preparing a pigment suspension comprising the pigment and a first water-soluble inorganic salt solution, wherein a pH of the pigment suspension is 7;
preparing a substrate suspension comprising the flake substrate;
adjusting the pH of the pigment suspension with a second water-soluble inorganic salt solution to 12;
preparing a mixture comprising the pigment suspension, a metal salt, and the substrate suspension, wherein a pH of the mixture is 5.5; and
allowing a reaction within the mixture to coat the substrate with the pigment,
wherein the flake substrate comprises at least one selected from the group consisting of synthetic mica, natural mica, glass, plate iron oxide, plate alumina, plate silica, talc and bismuth, and wherein the flake substrate comprises a metal oxide coating on a surface the flake substrate,
wherein the natural charcoal is at least any one selected from the group consisting of chestnut charcoal, *Quercus phillyraeoides* charcoal, Japanese larch charcoal, Japanese cedar charcoal, Japanese cypress charcoal, Yukari charcoal, mangrove charcoal, sasanqua charcoal, olive charcoal and acacia charcoal,
wherein the milling is performed at 20 to 40 Hz for 24 to 72 hours.

2. The production method of claim 1, further comprises, after preparing the pigment suspension, adjusting a pH of the pigment suspension to a neutral state, and wherein preparing the substrate suspension comprising preparing a suspension comprising the flake substrate and D.I. water.

3. The production method of claim 1, wherein in the preparing of the pigment suspension, a concentration of the pigment is adjusted to 5 to 30 wt % based on 100 wt % of the suspension.

4. The production method of claim 1, wherein in the forming of the substrate suspension, a concentration of the substrate is adjusted to 3 to 25 wt % based on 100 wt % of the suspension.

5. The production method of claim 1, wherein the metal salt comprises one selected from $BaCl_2$, $CaCl_2$, $AlCl_3$, $SnCl_4$, $TiCl_4$, $TiOCl_2$, $TiOSO_4$, $FeCl_3$, $FeSO_4$, $SiCl_4$, $ZrOCl_2$, $Na_2OSiO_2 5H_2O$, $MnCl_2$, $MgCl_2$, $CoCl_2$, or a mixture of one or more thereof.

6. The production method of claim 5, wherein a concentration of the metal salt is adjusted to 3 to 20 wt % based on 100 wt % of the substrate suspension.

7. The production method of claim 1, further comprising: after the coating of the flake substrate,
- washing the flake substrate by rinsing and dehydrating the flake substrate coated with the natural charcoal powder;
- drying the flake substrate by drying the washed flake substrate; and
- screening the flake substrate by separating the flake substrate formed larger than a predetermined size among the dried flake substrates, using a mesh.

8. The production method of claim 7, wherein in the screening of the flake substrate, an average particle size of the flake substrate to be separated is 45 µm or less.

* * * * *